United States Patent
Tsujioka et al.

(10) Patent No.: US 6,783,896 B2
(45) Date of Patent: Aug. 31, 2004

(54) ELECTROLYTE FOR ELECTROCHEMICAL DEVICE

(75) Inventors: Shoichi Tsujioka, Saitama (JP); Hironari Takase, Saitama (JP); Mikihiro Takahashi, Saitama (JP); Hiromi Sugimoto, Saitama (JP); Makoto Koide, Saitama (JP)

(73) Assignee: Central Glass Company, Limited, Yamaguchi (JP)

( * ) Notice: Subject to any disclaimer, the term of this patent is extended or adjusted under 35 U.S.C. 154(b) by 250 days.

(21) Appl. No.: 09/969,127

(22) Filed: Oct. 3, 2001

(65) Prior Publication Data

US 2002/0081496 A1 Jun. 27, 2002

(30) Foreign Application Priority Data

| Oct. 3, 2000 | (JP) | 2000-303437 |
| Dec. 12, 2000 | (JP) | 2000-376730 |
| Dec. 12, 2000 | (JP) | 2000-376731 |
| Jun. 13, 2001 | (JP) | 2001-177867 |

(51) Int. Cl.$^7$ .............. H01M 6/18; H01G 9/00
(52) U.S. Cl. ............ 429/306; 429/307; 429/322; 252/62.2; 361/502; 361/504; 361/505
(58) Field of Search .............. 429/306, 307, 429/322; 252/62.2; 361/502, 504, 505

(56) References Cited

U.S. PATENT DOCUMENTS 6,506,516 B1 * 1/2003 Wietelmann et al. ....... 429/188
6,548,212 B1 * 4/2003 Heider et al. ............... 429/307
2001/0033964 A1 * 10/2001 Heider et al. ............... 429/188

FOREIGN PATENT DOCUMENTS

| DE | 198 29 030 | * 10/1999 |
| EP | 1 035 612 | * 9/2000 |
| EP | 1074555 | 2/2001 |
| EP | 1075036 | 2/2001 |

* cited by examiner

*Primary Examiner*—Laura Weiner
(74) *Attorney, Agent, or Firm*—Crowell & Moring LLP

(57) ABSTRACT

The invention relates to an electrolyte for an electrochemical device. This electrolyte includes a first compound that is an ionic metal complex represented by the general formula (1). The electrolyte may further include at least one compound selected from second to sixth compounds respectively represented by the general formulas $A^{a+}(PF_6^-)_a$, $A^{a+}(ClO_4^-)_a$, $A^{a+}(BF_4^-)_a$, $A^{a+}(AsF_6^-)_a$, and $A^{a+}(SbF_6^-)_a$, and special seventh to twelfth compounds.

$$A^{2+}{}_p \left[ (R^2)_n - M \underset{X^2}{\overset{X^1}{<}} \underset{\underset{O}{\|}}{\overset{\overset{O}{\|}}{<}} (R^1)_q \right]^{b-}_m \quad (1)$$

The electrolyte can be superior in heat resistance, hydrolysis resistance, cycle characteristics and shelf life as compared with conventional electrolytes.

19 Claims, No Drawings

ELECTROLYTE FOR ELECTROCHEMICAL DEVICE

BACKGROUND OF THE INVENTION

The present invention relates to an electrolyte, an ion conductor including the electrolyte, and electrochemical devices including the electrolyte, such as lithium cells, lithium ion cells, electrical double-layer capacitors.

Accompanying the evolution of portable equipment in recent years, there has been active development of electrochemical devices utilizing electrochemical phenomena, such as cells for use as their power supplies and capacitors. In addition, electrochromic devices (ECD), in which a color change occurs due to an electrochemical reaction, are examples of electrochemical devices for uses other than power supplies.

These electrochemical devices are typically composed of a pair of electrodes and an ion conductor filled between them. The ion conductor contains a salt (AB) as an electrolyte, which is dissolved in a solvent, polymer or mixture thereof such that the salt is dissociated into cations ($A^+$) and anions ($B^-$), resulting in ionic conduction. In order to obtain the required level of ion conductivity for the device, it is necessary to dissolve a sufficient amount of this electrolyte in solvent or polymer. In actuality, there are many cases in which a solvent other than water is used, such as organic solvents and polymers. Electrolytes having sufficient solubility in such organic solvents and polymers are presently limited to only a few types. For example, electrolytes having sufficient solubility for use in lithium cells are only $LiClO_4$, $LiPF_6$, $LiBF_4$, $LiAsF_6$, $LiN(SO_2CF_3)_2$, $LiN(SO_2C_2F_5)_2$, $LiN(SO_2CF_3)(SO_2C_4F_9)$ and $LiCF_3SO_3$. Although the cation type of the electrolyte is frequently limited by the device as is the case with the lithium ion of lithium cells, any anion can be used for the electrolyte provided it satisfies the condition of having high solubility.

Amidst the considerable diversity of the application range of these devices, efforts are made to seek out the optimum electrolyte for each application. Under the present circumstances, however, optimization efforts have reached their limit due to the limited types of available anions. In addition, existing electrolytes have various problems, thereby creating the need for an electrolyte having a novel anion portion. More specifically, since $ClO_4$ ion of $LiClO_4$ is explosive and $AsF_6$ ion of $LiAsF_6$ is toxic, they cannot be used for reasons of safety. Even the only practical electrolyte of $LiPF_6$ has problems including heat resistance and hydrolysis resistance. Although electrolytes of $LiN(CF_3SO_2)_2$, $LiN(SO_2C_2F_6)_2$, $LiN(SO_2CF_3)(SO_2C_4F_9)$ and $LiCF_3SO_3$ are stable and high in ionic conductivity, they corrode the aluminum collector inside the cell when a potential is applied. Therefore, their use presents difficulties.

SUMMARY OF THE INVENTION

It is therefore an object of the present invention to provide a useful novel electrolyte, a novel ion conductor containing the electrolyte, and a novel electrochemical device containing the ion conductor.

According to the present invention, there is provided an electrolyte for an electrochemical device. This electrolyte comprises a first compound that is an ionic metal complex represented by the general formula (1),

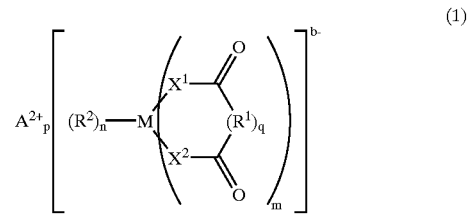

wherein M is a transition metal selected from the group consisting of elements of groups 3–11 of the periodic table, or an element selected from the group consisting of elements of groups 12–15 of the periodic table;

$A^{a+}$ represents a metal ion, onium ion or hydrogen ion;

a represents a number from 1 to 3; b represents a number from 1 to 3; p is b/a; m represents a number from 1 to 4; n represents a number from 1 to 8; q is 0 or 1;

$R^1$ represents a $C_1$–$C_{10}$ alkylene group, $C_1$–$C_{10}$ halogenated alkylene group, $C_4$–$C_{20}$ arylene group or $C_4$–$C_{20}$ halogenated arylene group, these alkylene and arylene groups of said $R^1$ optionally having substituents and hetero atoms, one of said $R^1$ being optionally bonded with another of said $R^1$;

$R^2$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^3R^3$, these alkyl and aryl groups of said $R^2$ optionally having substituents and hetero atoms, one of said $R^2$ being optionally bonded with another of said $R^2$ to form a ring;

each of $X^1$, $X^2$ and $X^3$ independently represents O, S or $NR^4$; and each of $R^3$ and $R^4$ independently represents a halogen, $C_1$–$C_{10}$ alkyl group, $C_1$–$C_{10}$ halogenated alkyl group, $C_4$–$C_{20}$ aryl group, or $C_4$–$C_{20}$ halogenated aryl group, these alkyl and aryl groups of said $R^3$ and $R^4$ optionally having substituents and hetero atoms, one of said $R^3$ being optionally bonded with another of said $R^3$ to form a ring, one of said $R^4$ being optionally bonded with another of said $R^4$ to form a ring.

According to the present invention, there is provided an ion conductor for an electrochemical device. This ion conductor comprises the electrolyte; and a member selected from the group consisting of a nonaqueous solvent, a polymer and a mixture thereof, said member dissolving therein said electrolyte.

According to the present invention, there is provided an electrochemical device comprising (a) first and second electrodes; and (b) the ion conductor receiving therein said first and second electrodes.

DESCRIPTION OF THE PREFERRED EMBODIMENTS

According to the invention, the alkyl groups, halogenated alkyl groups, aryl groups, halogenated aryl groups, alkylene groups, halogenated alkylene groups, arylene groups and halogenated arylene groups which are contained in the ionic metal complex and the raw materials for synthesizing the same, may be branched and/or may have other functional groups such as hydroxyl groups and ether bonds.

The followings are specific six examples of the ionic metal complex represented by the general formula (1) of the present invention.

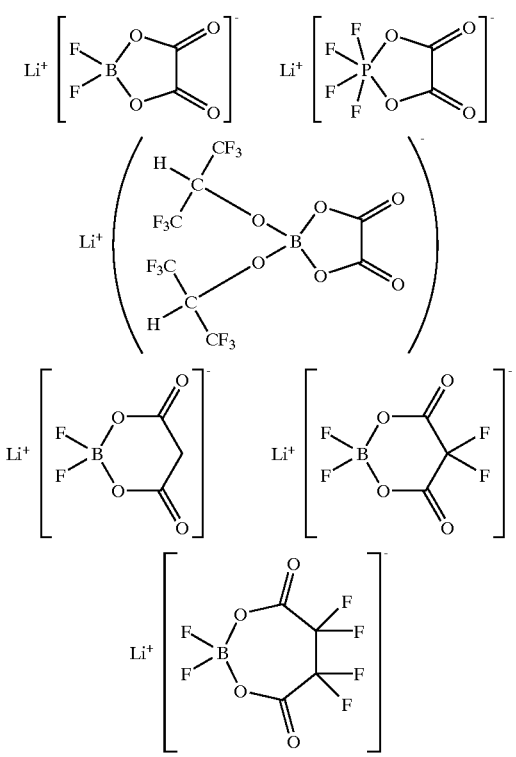

Here, although lithium ion is indicated as an example of $A^{a+}$ of the general formula (1), examples of other cations that can be used other than lithium ion include sodium ion, potassium ion, magnesium ion, calcium ion, barium ion, cesium ion, silver ion, zinc ion, copper ion, cobalt ion, iron ion, nickel ion, manganese ion, titanium ion, lead ion, chromium ion, vanadium ion, ruthenium ion, yttrium ion, lanthanoid ion, actinoid ion, tetrabutylammonium ion, tetraethylammonium ion, tetramethylammonium ion, triethylmethylammonium ion, triethylammonium ion, pyridinium ion, imidazolium ion, hydrogen ion, tetraethylphosphonium ion, tetramethylphosphonium ion, tetraphenylphosphonium ion, triphenylsulfonium ion, and triethylsulfonium ion. In the case of considering the application of the ionic metal complex for electrochemical devices and the like, lithium ion, tetraalkylammonium ion and hydrogen ion are preferable. As shown in the general formula (1), the valency (valence) of the $A^{a+}$ cation is preferably from 1 to 3. If the valency is larger than 3, the problem occurs in which it becomes difficult to dissolve the ionic metal complex in solvent due to the increase in crystal lattice energy. Consequently, in the case of requiring solubility of the ionic metal complex, a valency of 1 is preferable. As shown in the general formula (1), the valency ($b^-$) of the anion is similarly preferably from 1 to 3, and a valency of 1 is particularly preferable. The constant p expresses the ratio of the valency of the anion to the valency of the cation, namely b/a.

In the general formula (1), M at the center of the ionic metal complex of the present invention is selected from elements of groups 3–15 of the periodic table. It is preferably Al, B, V, Ti, Si, Zr, Ge, Sn, Cu, Y, Zn, Ga, Nb, Ta, Bi, P, As, Sc, Hf or Sb, and more preferably Al, B or P. Although it is possible to use various elements for the M other than these preferable examples, synthesis is relatively easy in the case of using Al, B, V, Ti, Si, Zr, Ge, Sn, Cu, Y, Zn, Ga, Nb, Ta, Bi, P, As, Sc, Hf or Sb. In addition to ease of synthesis, the ionic metal complex has excellent properties in terms of low toxicity, stability and production cost in the case of using Al, B or P.

In the general formula (1), the organic or inorganic portion bonded to M is referred to as the ligand.

In the general formula (1), $R^1$ is selected from $C_1$–$C_{10}$ alkylene groups, $C_1$–$C_{10}$ halogenated alkylene groups, $C_4$–$C_{20}$ arylene groups and $C_4$–$C_{20}$ halogenated arylene groups. These alkylene and arylene groups may have substituents and hetero atoms in their structures. For example, the alkylene and arylene groups may have structures in which hydrogen has been replaced with a substituent selected from halogens, chain-like or cyclic alkyl groups, aryl groups, alkenyl groups, alkoxy groups, aryloxy groups, sulfonyl groups, amino groups, cyano groups, carbonyl groups, acyl groups, amide groups and hydroxyl group. Furthermore, they may have structures in which carbon has been replaced with a substituent selected from nitrogen, sulfur and oxygen. When $R^1$ exist in the plural number, they may be bonded together. For example, a ligand such as ethylenediaminetetraacetic acid can be cited.

In the general formula (1), $R^2$ is selected from halogens, $C_1$–$C_{10}$ alkyl groups, $C_1$–$C_{10}$ halogenated alkyl groups, $C_4$–$C_{20}$ aryl groups, $C_4$–$C_{20}$ halogenated aryl groups and $X^3R^3$. Similar to $R^1$, these alkyl and aryl groups may have substituents and hetero atoms in their structures. When $R^2$ exist in the plural number, they may be bonded together to form a ring. $R^2$ is preferably an electron attracting group, particularly fluorine. When $R^2$ is fluorine, the degree of dissociation of the electrolyte is improved due to its strong electron attraction. Furthermore, mobility of the electrolyte is also improved due to the reduced size of the anionic moiety of the electrolyte. Therefore, the ionic conductivity becomes very high when R2 is fluorine.

As mentioned above, each of $X^1$, $X^2$ and $X^3$ in the general formula (1) independently represents O, S or $NR^4$. Thus, the ligands are bonded to M with an interposal of these hetero atoms (O, S and N) therebetween. Although the bonding of an atom other than O, S or N is not impossible, the synthesis becomes extremely bothersome. The ionic metal complex represented by the general formula (1) is characterized by these ligands forming a chelate structure with M since there is bonding with M by $X^1$ and $X^2$ within the same ligand. As a result of this chelation, the heat resistance, chemical stability and hydrolysis resistance of the ionic metal complex are improved. Although constant q in this ligand is either 0 or 1, in the case of 0 in particular, since the chelate ring becomes a five-member ring, chelating effects are demonstrated most prominently, making this preferable due to the resulting increase in stability.

In the general formula (1), each of $R^3$ and $R^4$ independently represents a halogen, $C_1$–$C_{10}$ alkyl group, $C_1$–$C_{10}$ halogenated alkyl group, $C_4$–$C_{20}$ aryl group, or $C_4$–$C_{20}$ halogenated aryl group. These alkyl and aryl groups optionally have substituents and hetero atoms. When $R^3$ and $R^4$ are each exist in the plural number, each of $R^3$ and $R^4$ may be formed into a ring.

In the general formula (1), the values of the constants m and n relating to the number of the above-mentioned ligands depend on the type of the central M. In fact, m is preferably from 1 to 4, while n is preferably from 1 to 8.

The anion of the ionic metal complex represented by the general formula (1) is stabilized by having therein carbonyl group (C=O group) with strong electron attraction, thereby facilitating dissociation of the ionic metal complex into the anion and cation. This is extremely important in the case of using as the electrolyte of an electrochemical device. Although there are an almost infinite number of salts referred to as electrolytes, the majority dissolve and dissociate in water, and thereby are ion conductive. Many of such salts do not even dissolve in organic solvents and so forth other than water. Such aqueous solutions are used as an electrolytic solution of electrochemical devices. However, due to the low decomposition potential of water as a solvent and its susceptibility to oxidation and reduction, there are many restrictions on its use. For example, in a lithium cell and so forth, since the potential difference between the electrodes of the device is 3 V or more, water ends up being electrolyzed into hydrogen and oxygen. There are many organic solvents and polymers that are insusceptible to oxidation and reduction as compared with water due to their structures. Therefore, they are used in devices requiring higher voltages such as lithium cells and electrical double-layer capacitors.

In comparison with conventional electrolytes, the electrolyte of the present invention is extremely soluble in organic solvent and dissociates more easily due to the above-mentioned effects of C=O groups and a large size of the anion of the ionic metal complex. Consequently, an electrolytic solution containing an electrolyte of the ionic metal complex dissolved in an organic solvent can be used as a superior ion conductor of electrochemical devices such as lithium cells. Complexes of organic substances and metals are typically susceptible to hydrolysis and there are many that are chemically unstable. Since the electrolyte of the present invention, however, has a chelate structure, it is extremely stable and resistant to hydrolysis and so forth. In addition, that having fluorine within the chemical structure represented by the general formula (1) is particularly preferable since it further increases chemical stability such as oxidation resistance due to the effect of the fluorine.

Optimization of the chemical structure of the general formula (1) makes it possible to obtain an electrolyte that dissolves in organic solvents in which conventional electrolytes do not dissolve, examples of which include toluene, hexane and fluorine-containing organic solvents such as fluorohydrocarbons.

Although the electrolyte of the present invention is used as the electrolyte of electrochemical devices such as lithium cells (cells), lithium ion cells (cells) and electrical double-layer capacitors, examples of its other applications include catalysts of organic synthesis reactions, polymerization catalysts and co-catalysts (auxiliary catalysts) of olefin polymerization.

There are no particular restrictions on the process for synthesizing the ionic metal complex of the present invention. For example, an ionic metal complex (electrolyte) having the following formula can be synthesized by reacting in a nonaqueous solvent $LiBF_4$ with a lithium alkoxide in an amount (by mole) that is twice that of $LiBF_4$, followed by addition of oxalic acid, thereby replacing the alkoxide bonded to boron with oxalic acid.

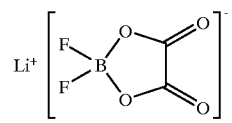

According to a first preferred embodiment of the invention, the electrolyte contains the ionic metal complex represented by the general formula (1). This electrolyte can be superior in heat resistance and hydrolysis resistance as compared with conventional electrolytes. Thus, it can advantageously be used for electrochemical devices such as lithium cell, lithium ion cell and electrical double-layer capacitor.

According to a second preferred embodiment of the invention, the electrolyte contains the ionic metal complex (first compound) represented by the general formula (1) and another component that is at least one compound selected from second to sixth compounds respectively represented by the general formulas $A^{a+}(PF_6^-)_a$, $A^{a+}(ClO_4^-)_a$, $A^{a+}(BF_4^-)_a$, $A^{a+}(AsF_6^-)_a$, and $A^{a+}(SbF_6^-)_a$, where $A^{a+}$ is preferably the same ion as that in the general formula (1). If the ionic metal complex is omitted in the second preferred embodiment, the following problem occurs. That is, the anion(s) tends to be pyrolyzed at a high temperature of 60° C. or higher, thereby generating a Lewis acid(s). This Lewis acid decomposes the solvent and makes the electrochemical device inferior in performance and lifetime. Furthermore, the omission of the ionic metal complex causes hydrolysis of the anion(s) when the electrolyte is contaminated with a very small amount of water. This hydrolysis generates an acid(s) that makes the electrochemical device inferior in performance and lifetime. In contrast, according to the second preferred embodiment, the above-mentioned pyrolysis and hydrolysis can unexpectedly be prevented by using a mixture of the ionic metal complex and the another component. The reason of this is not clear. It is, however, assumed that the properties of the solution as a whole change somehow to achieve this prevention by a certain interaction between the ionic metal complex and the another component.

According to a third preferred embodiment of the invention, the electrolyte contains the ionic metal complex (first compound) represented by the general formula (1) and another component that is at least one compound selected from seventh to ninth compounds represented by the general formulas (2), (3) and (4).

(2)

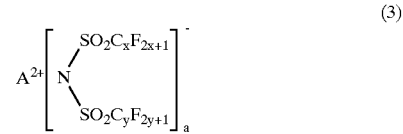

(3)

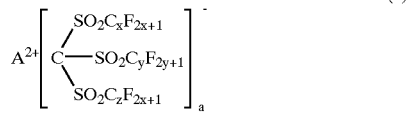

(4)

Examples of these compounds are $LiCF_3SO_3$, $LiN(SO_2CF_3)_2$, $LiN(SO_2C_2F_5)_2$, $LiN(SO_2CF_3)(SO_2C_4F_9)$ and $LiC(SO_2CF_3)_3$. If the ionic metal complex is omitted in the third preferred embodiment, the following problem occurs. That is, the another component corrodes the aluminum collector inside the cell when a potential is applied. With this, the capacity is lowered by repeating the charge and discharge cycle. In contrast, according to the third preferred embodiment, the aluminum collector corrosion can unexpectedly be prevented by using a mixture of the ionic metal complex and the another component. The reason of this is not clear. It is, however, assumed that the ionic metal complex is slightly decomposed on the electrode surface and that a film of the ionic metal complex's ligand is formed on the aluminum surface, thereby preventing the aluminum collector corrosion.

According to a fourth preferred embodiment of the invention, the electrolyte contains the ionic metal complex (first compound) represented by the general formula (1) and another component that is at least one compound selected from the above-mentioned tenth to twelfth compounds represented by the general formulas (5), (6) and (7).

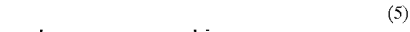

(5)

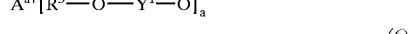

(6)

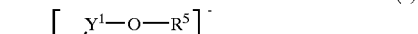

(7)

Examples of these compounds are $CF_3CH_2OSO_3Li$, $(CF_3)_2CHOSO_3Li$, $(CF_3CH_2OSO_2)_2NLi$, $((CF_3)_2CHO SO_2)_2NLi$, $(CF_3CH_2OSO_2)((CF_3)_2CHOSO_2)NLi$, $((CF_3)_2COSO_2)_2NLi$, and $((CF_3)_2CHOSO_2)_3CLi$. Further examples are polymers and oligomers such as $[N(Li) SO_2OCH_2(CF_2)_4CH_2OSO_2]_n$, where n is a number of 2–1,000. If the ionic metal complex is omitted in the fourth preferred embodiment, the following problem occurs. That is, the another component corrodes the aluminum collector inside the cell when a potential is applied. With this, the capacity is lowered by repeating the charge and discharge cycle. In contrast, according to the fourth preferred embodiment, the aluminum collector corrosion can unexpectedly be prevented by using a mixture of the ionic metal complex and the another component. The reason of this is not clear. It is, however, assumed that the ionic metal complex is slightly decomposed on the electrode surface and that a film of the ionic metal complex's ligand is formed on the aluminum surface, thereby preventing the aluminum collector corrosion.

The electrolytes according to the second to fourth preferred embodiments can be superior in cycle characteristics and shelf life as compared with conventional electrolytes. Thus, they can advantageously be used for electrochemical devices such as lithium cell, lithium ion cell and electrical double-layer capacitor.

In the invention, the molar ratio of the ionic metal complex (first compound) to the at least one compound selected from the second to twelfth compounds is preferably 1:99 to 99:1 (or a range from 5:95 to 95:5), more preferably 20:80 to 80:20 (or a range from 30:70 to 70:30), in view of improving the electrochemical device in cycle characteristics and shelf life. If this ratio is less than 1:99 (or 5:95), it may become insufficient to prevent the above-mentioned aluminum corrosion and/or the above-mentioned pyrolysis and hydrolysis, thereby making the electrolyte inferior in cycle characteristics and shelf life. If the ratio is greater than 99:1 (or 95:5), advantages of adding the at least one compound to increase ionic conductivity and electrochemical stability may become insufficient.

In the case of preparing an electrochemical device of the present invention, its basic structural elements are ion conductor, negative electrode, positive electrode, collector, separator, container and the like.

A mixture of electrolyte and non-aqueous solvent or polymer is used as the ion conductor. If a non-aqueous solvent is used, the resulting ion conductor is typically referred to as an electrolytic solution, while if a polymer is used, it is typically referred to as a polymer solid electrolyte. Non-aqueous solvent may also be contained as plasticizer in polymer solid electrolytes.

There are no particular restrictions on the non-aqueous solvent provided it is an aprotic solvent that is able to dissolve an electrolyte of the present invention, and examples of this non-aqueous solvent that can be used include carbonates, esters, ethers, lactones, nitrites, amides and sulfones. In addition, the solvent can either be used alone or in the form of a mixture of two or more types of solvent. Specific examples of the solvent include propylene carbonate, ethylene carbonate, diethyl carbonate, dimethyl carbonate, methylethyl carbonate, dimethoxyethane, acetonitrile, propionitrile, tetrahydrofuran, 2-methyltetrahydrofuran, dioxane, nitromethane, N,N-dimethylformamide, dimethylsulfoxide, sulfolane and γ-butyrolactone.

In case that $A^{a+}$ of the general formula (1) is lithium ion, the non-aqueous solvent of an electrolytic solution is preferably a mixture of a first aprotic solvent having a dielectric constant of 20 or greater and a second aprotic solvent having a dielectric constant of 10 or less. In fact, lithium salt has a low solubility in the second aprotic solvent (e.g., diethyl ether and dimethyl carbonate). Therefore, it may be difficult to obtain a sufficient ionic conductivity by using only the second aprotic solvent. In contrast, lithium salt has a high solubility in the first aprotic solvent. The resulting solution is, however, high in viscosity. Thus, it may be difficult to obtain a sufficient ionic conductivity by using only the first aprotic solvent, too. In contrast, it becomes possible to gain a suitable solubility and a suitable ionic mobility by using a mixture of the first and second aprotic solvents, thereby making it possible to obtain a sufficient ionic conductivity.

There are no particular restrictions on the polymer to be mixed with the electrolytes of the invention provided it is an aprotic polymer. Examples of such polymer include polymers having polyethylene oxide on their main chain or side chain, homopolymers or copolymers of polyvinylidene fluoride, methacrylate polymers and polyacrylonitrile. In the case of adding plasticizer to these polymers, the above-mentioned aprotic non-aqueous solvent can be used. The total concentration of the electrolytes of the present invention in these ion conductors is preferably 0.1 $mol/dm^3$ or more up to the saturated concentration, and more preferably from 0.5 $mol/dm^3$ to 1.5 $mol/dm^3$. If the concentration is lower than 0.1 $mol/dm^3$, ion conductivity may become too low.

There are no particular restrictions on the negative electrode material for preparing an electrochemical device. In the case of lithium cell, lithium metal (metallic lithium) or an alloy of lithium and another metal can be used. In the case of a lithium ion cell, it is possible to use an intercalation compound containing lithium atoms in a matrix of another material, such as carbon, natural graphite or metal oxide. This carbon can be obtained by baking polymer, organic substance, pitch or the like. In the case of electrical double-layer capacitor, it is possible to use activated carbon, porous metal oxide, porous metal, conductive polymer and so forth.

There are no particular restrictions on the positive electrode material. In the case of lithium cell or lithium ion cell, lithium-containing oxides such as $LiCoO_2$, $LiNiO_2$, $LiMnO_2$ and $LiMn_2O_4$; oxides such as $TiO_2$, $V_2O_5$ and $MoO_3$; sulfides such as $TiS_2$ and FeS; and electrically conductive polymers such as polyacetylene, polyparaphenylene, polyaniline or polypyrrole can be used. In the case of electrical double-layer capacitor, activated carbon, porous metal oxide, porous metal, electrically conductive polymer and so forth can be used.

The following nonlimitative examples are illustrative of the present invention. In fact, Examples 1-1 to 1-4 are illustrative of the above-mentioned first preferred embodiment, and Examples 2-1 to 2-5 are illustrative of the above-mentioned second preferred embodiment, Examples 3-1 to 3-5 are illustrative of the above-mentioned third preferred embodiment, and Examples 4-1 to 4-4 are illustrative of the above-mentioned fourth preferred embodiment.

EXAMPLE 1-1

1.37 g of lithium tetrafluoroborate were dissolved in 10 ml of acetonitrile at room temperature. To the resulting solution 5.09 g of lithium hexafluoroisopropoxide ($LiOCH(CF_3)_2$) were slowly added. Then, the reaction was conducted at 60° C. for 3 hr with stirring. With this, lithium fluoride was precipitated. To the obtained reaction liquid 1.31 g of oxalic acid were added, and the reaction was conducted at 60° C. for 1 hr with stirring. Then, the lithium fluoride was separated from the reaction liquid by filtration. Then, the solvent was distilled out of the obtained filtrate at 60° C. under a vacuum condition of $10^{-1}$ Pa, thereby obtaining 1.90 g of a white solid. This solid was dried at 100° C. for 24 hr under vacuum condition of $10^{-1}$ Pa, thereby obtaining 1.90 g of lithium difluoro(oxalato)borate (yield: 91%) represented by the following formula. The product was identified by elemental analysis.

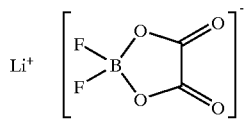

The NMR spectrum of lithium difluoro(oxalato)borate is as follows.

$^{19}$F-NMR (standard: $C_6F_6$; solvent: $CD_3CN$) 10.4 ppm(s)
$^{11}$B-NMR (standard: $B(OCH_3)_3$; solvent: $CD_3CN$) −15.7 ppm(s)
$^{13}$C-NMR (standard: $D_2O$) 164.7 ppm

EXAMPLE 1-2

The compound obtained in Example 1-1 was dissolved in a mixed solution of ethylene carbonate (EC) and dimethyl carbonate (DMC) (EC:DMC=1:1) to prepare an electrolytic solution having an electrolyte concentration of 1 mol/dm³ followed by measurement of ion conductivity with an alternating current bipolar-type cell. As a result, the ion conductivity was 8.6 mS/cm.

The above-mentioned electrolyte was placed in a container made of fluororesin. When stored for 1 month at 100° C. as a heat resistance test, there was no discoloration or other deterioration of the electrolytic solution. In addition, when water was added to this electrolytic solution, it was found by NMR that the electrolytic solution had not been subjected to hydrolysis at all.

A corrosion test of an aluminum collector was performed using the above-mentioned electrolytic solution. A beaker type cell was used for the test cell, using aluminum for the working electrode, and lithium metal (metallic lithium) for the counter electrode and reference electrode. When the working electrode was held at 5 V (Li/Li⁺), there was no flow of current whatsoever. Following testing, although the surface of the working electrode was observed by SEM, there were no changes observed in comparison with that before testing.

EXAMPLE 1-3

A charging and discharging test of an actual cell was performed using the above-mentioned electrolytic solution of Example 1-2. The test cell was prepared in the manner described below. The positive electrode was prepared by mixing together 90 wt % of an $LiCO_2$ powder, 5 wt % of polyvinylidene fluoride (PVDF) as a binder, and 5 wt % of acetylene black as a conductor, followed by the addition of N,N-dimethylformamide to form a paste. This paste was applied to an aluminum foil and allowed to dry to obtain the test positive electrode. Lithium metal was used for the negative electrode. A glass fiber filter as a separator was impregnated with the electrolytic solution of Example 1-2, thereby assembling the cell.

Next, a constant current charging and discharging test was conducted as described below. The current density was 0.35 mA/cm² for both charging and discharging, while charging was performed until 4.2 V and discharging until 3.0 V (vs. Li/Li⁺). As a result, the initial discharge capacity was 125 mAh/g. Although charging and discharging were repeated 20 times, results were obtained in which the capacity of the 20$^{th}$ cycle was 88% of the initial capacity.

EXAMPLE 1-4

A charging and discharging test of an actual cell was conducted using the electrolytic solution of Example 1-2. The test cell (half cell) was prepared in the manner described below. 10 wt % of polyvinylidene fluoride (PVDF) as a binder were mixed with 90 wt % of natural graphite powder followed by the addition of N,N-dimethylformamide to prepare a slurry. This slurry was applied to a nickel mesh and allowed to dry for 12 hours at 150° C. to prepare a test negative electrode. Lithium metal was used for a counter electrode. A glass fiber filter as a separator was impregnated with the above-mentioned electrolytic solution, thereby assembling the half cell.

A constant current charging and discharging test was then conducted under the conditions indicated below. The current density was 0.3 mA/cm² for both charging and discharging, while charging was performed until 0.0 V and discharging until 1.5 V (vs. Li/Li⁺). As a result, the initial discharge capacity was 320 mAh/g. Although charging and discharging were repeated 20 times, results were obtained in which the capacity of the 20$^{th}$ cycle was 95% of the initial capacity.

COMPARATIVE EXAMPLE 1-1

$LiPF_6$ was dissolved in a mixed solvent of ethylene carbonate (EC) and dimethyl carbonate (DMC) (EC:DMC=1:1) to prepare an electrolytic solution having an electrolyte concentration of 1 mol/dm³. Next, this electrolytic solution was placed in a fluororesin container, and, when subjected to a heat resistance test by storing for 1 month at 100° C., the electrolytic solution changed to have a yellow color.

When water was added to this electrolytic solution prior to conducting the heat resistance test, various hydrolysis products were found by NMR. Substances detected as hydrolysis products included hydrogen fluoride and phosphorus oxychloride.

COMPARATIVE EXAMPLE 1-2

$LiN(CF_3SO_2)_2$ was dissolved in a mixed solvent of ethylene carbonate (EC) and dimethyl carbonate (DMC)

(EC:DMC=1:1) to prepare an electrolytic solution having an electrolyte concentration of 1 mol/dm$^3$. Next, a corrosion test of an aluminum separator was conducted using this electrolyte. A beaker type cell was used for the test cell, using aluminum for the working electrode, and lithium metal for the counter electrode and reference electrode. When the working electrode was held at 5 V (Li/Li$^+$), current flowed and the current value increased with time. Following testing, when the surface of the working electrode was observed by SEM, severe corrosion pits were found in the aluminum surface.

EXAMPLE 2-1

A lithium borate derivative, represented by the following formula, and LiPF$_6$ were dissolved in a mixture of ethylene carbonate (EC) and dimethyl carbonate (DMC) (EC:DMC= 1:1 by volume) to prepare an electrolytic solution having a lithium borate derivative concentration of 0.05 mol/liter and a LiPF$_6$ concentration of 0.95 mol/liter.

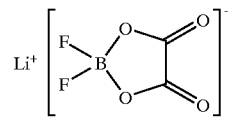

A charging and discharging test of an actual cell was conducted using the above-mentioned electrolytic solution. The test cell was prepared in the manner described below. The positive electrode of LiCoO$_2$ was prepared by mixing 5 parts by weight of polyvinylidene fluoride (PVDF) as a binder and 5 parts by weight of acetylene black as a conductor with 90 parts by weight of a LiCoO$_2$ powder followed by the addition of N,N-dimethylformamide to form a paste. This paste was applied to an aluminum foil and allowed to dry to obtain the test positive electrode. The negative electrode of natural graphite was prepared by mixing 10 parts by weight of polyvinylidene fluoride (PVDF) as a binder with 90 parts by weight of a natural graphite powder followed by the addition of N,N-dimethylformamide to form a slurry. This slurry was applied to an copper foil and allowed to dry at 150° C. for 12 hr to obtain the test negative electrode. A polyethylene separator was impregnated with the electrolytic solution, thereby assembling the cell.

Next, a constant current charging and discharging test was conducted at 70° C. under the following conditions. The current density was 0.35 mA/cm$^2$ for both charging and discharging, while charging was performed until 4.2 V and discharging until 3.0 V (vs. Li/Li$^+$). Although charging and discharging were repeated 500 times, results were obtained in which the capacity of the 500$^{th}$ cycle was 85% of the initial capacity.

EXAMPLE 2-2

The lithium borate derivative of Example 2-1 and LiPF$_6$ were dissolved in a mixture of propylene carbonate (PC) and diethyl carbonate (DEC) (PC:DEC=1:1 by volume) to prepare an electrolytic solution having a lithium borate derivative concentration of 0.10 mol/liter and a LiPF$_6$ concentration of 0.90 mol/liter.

The test cell was prepared in the same manner as that of Example 2-1, and a constant current charging and discharging test was conducted in the same manner as that of Example 2-1. As a result, although charging and discharging were repeated 500 times, results were obtained in which the capacity of the 500th cycle was 83% of the initial capacity.

EXAMPLE 2-3

The lithium borate derivative of Example 2-1 and LiBF$_4$ were dissolved in a mixture of ethylene carbonate (EC) and dimethyl carbonate (DMC) (EC:DMC =1:1 by volume) to prepare an electrolytic solution having a lithium borate derivative concentration of 0.05 mol/liter and a LiBF$_4$ concentration of 0.95 mol/liter.

The test cell was prepared in the same manner as that of Example 2-1, and a constant current charging and discharging test was conducted in the same manner as that of Example 2-1. As a result, although charging and discharging were repeated 500 times, results were obtained in which the capacity of the 500$^{th}$ cycle was 80% of the initial capacity.

EXAMPLE 2-4

The lithium borate derivative of Example 2-1 and LiBF$_4$ were dissolved in a mixture of ethylene carbonate (EC) and dimethyl carbonate (DMC) (EC:DMC=1:1 by volume) to prepare an electrolytic solution having a lithium borate derivative concentration of 0.95 mol/liter and a LiBF$_4$ concentration of 0.05 mol/liter.

The test cell was prepared in the same manner as that of Example 2-1, and a constant current charging and discharging test was conducted in the same manner as that of Example 2-1. As a result, although charging and discharging were repeated 500 times, results were obtained in which the capacity of the 500$^{th}$ cycle was 85% of the initial capacity.

EXAMPLE 2-5

A solution was prepared by adding acetonitrile to 80 parts by weight of a polyethylene oxide (average molecular weight: 10,000). Then, 10 parts by weight of the lithium borate derivative of Example 2-1, and 10 parts by weight of LiPF$_6$ were added to the solution. The resulting mixture was cast on a glass, followed by drying to remove the acetonitrile. With this, a polymer solid electrolyte film was prepared.

The test cell was prepared in the same manner as that of Example 2-1 except in that the polymer solid electrolyte film was used in place of the electrolytic solution and the separator. In fact, LiCoO$_2$ was used as a positive electrode material, and natural graphite was used as a negative electrode material. A constant current charging and discharging test was conducted at 70° C. under the following conditions. The current density was 0.1 mA/cm$^2$ for both charging and discharging, while charging was performed until 4.2 V and discharging until 3.0 V (vs. Li/Li$^+$). As a result, the initial discharge capacity was 120 mAh/g (the positive electrode capacity). Although charging and discharging were repeated 500 times, results were obtained in which the capacity of the 500$^{th}$ cycle was 87% of the initial capacity.

COMPARATIVE EXAMPLE 2-1

At first, LiPF$_6$ was dissolved in a mixture of ethylene carbonate (EC) and dimethyl carbonate (DMC) (EC:DMC= 1:1 by volume) to prepare an electrolytic solution having a LiPF$_6$ concentration of 1.0 mol/liter.

The test cell was prepared in the same manner as that of Example 2-1, and a constant current charging and discharging test was conducted in the same manner as that of Example 2-1. The capacity of the 500$^{th}$ cycle was 64% of the initial capacity.

COMPARATIVE EXAMPLE 2-2

At first, LiBF$_4$ was dissolved in a mixture of ethylene carbonate (EC) and dimethyl carbonate (DMC) (EC:DMC=

1:1 by volume) to prepare an electrolytic solution having a LiBF$_4$ concentration of 1.0 mol/liter.

The test cell was prepared in the same manner as that of Example 2-1, and a constant current charging and discharging test was conducted in the same manner as that of Example 2-1. The capacity of the 500$^{th}$ cycle was 46% of the initial capacity.

EXAMPLE 3-1

The lithium borate derivative of Example 2-1 and LiN(SO$_2$C$_2$F$_5$)$_2$ were dissolved in a mixture of ethylene carbonate (EC) and dimethyl carbonate (DMC) (EC:DMC=1:1 by volume) to prepare an electrolytic solution having a lithium borate derivative concentration of 0.05 mol/liter and a LiN(SO$_2$C$_2$F$_5$)$_2$ concentration of 0.95 mol/liter. Then, ion conductivity of the electrolytic solution was measured with an alternating current bipolar-type cell. As a result, the ion conductivity was 7.2 mS/cm at 25° C.

A corrosion test of an aluminum collector was performed in the same manner as that of Example 1-2. When the working electrode was held at 5 V (Li/Li$^+$), there was no flow of current whatsoever. Following testing, although the surface of the working electrode was observed by SEM, there were no changes observed in comparison with that before testing.

A charging and discharging test of an actual cell was conducted using the above-mentioned electrolytic solution. The test cell (half cell) was prepared in the manner described below. The positive electrode was prepared by mixing 5 parts by weight of polyvinylidene fluoride (PVDF) as a binder and 5 parts by weight of acetylene black as a conductor with 90 parts by weight of a LiCoO$_2$ powder followed by the addition of N,N-dimethylformamide to form a paste. This paste was applied to an aluminum foil and allowed to dry to obtain the test positive electrode. Lithium metal was used for the negative electrode. A glass fiber filter as a separator was impregnated with the electrolytic solution, thereby assembling the cell.

Next, a constant current charging and discharging test was conducted as described below. The current density was 0.35 mA/cm$^2$ for both charging and discharging, while charging was performed until 4.2 V and discharging until 3.0 V (vs. Li/Li$^+$). As a result, the initial discharge capacity was 118 mAh/g (the positive electrode capacity). Although charging and discharging were repeated 100 times, results were obtained in which the capacity of the 100$^{th}$ cycle was 95% of the initial capacity.

EXAMPLE 3-2

The lithium borate derivative of Example 2-1 and LiN(SO$_2$CF$_3$)$_2$ were dissolved in a mixture of propylene carbonate (PC) and diethyl carbonate (DEC) (PC:DEC=1:1 by volume) to prepare an electrolytic solution having a lithium borate derivative concentration of 0.10 mol/liter and a LiN(SO$_2$CF$_3$)$_2$ concentration of 0.90 mol/liter. Then, ion conductivity of the electrolytic solution was measured with an alternating current bipolar-type cell. As a result, the ion conductivity was 8.8 mS/cm at 25° C.

A corrosion test of an aluminum collector was performed in the same manner as that of Example 1-2. When the working electrode was held at 5 V (Li/Li$^+$), there was no flow of current whatsoever. Following testing, although the surface of the working electrode was observed by SEM, there were no changes observed in comparison with that before testing.

The test cell (half cell) was prepared in the same manner as that of Example 3-1, and a constant current charging and discharging test was conducted in the same manner as that of Example 3-1. As a result, the initial discharge capacity was 115 mAh/g (the positive electrode capacity). Although charging and discharging were repeated 100 times, results were obtained in which the capacity of the 100$^{th}$ cycle was 88% of the initial capacity.

EXAMPLE 3-3

The lithium borate derivative of Example 2-1 and LiN(SO$_2$CF$_3$)(SO$_2$C$_4$F$_9$) were dissolved in a mixture of ethylene carbonate (EC) and dimethyl carbonate (DMC) (EC:DMC=1:1 by volume) to prepare an electrolytic solution having a lithium borate derivative concentration of 0.05 mol/liter and a LiN(SO$_2$CF$_3$)(SO$_2$C$_4$F$_9$) concentration of 0.95 mol/liter. Then, ion conductivity of the electrolytic solution was measured with an alternating current bipolar-type cell. As a result, the ion conductivity was 6.5 mS/cm at 25° C.

A corrosion test of an aluminum collector was performed in the same manner as that of Example 1-2. When the working electrode was held at 5 V (Li/Li$^+$), there was no flow of current whatsoever. Following testing, although the surface of the working electrode was observed by SEM, there were no changes observed in comparison with that before testing.

The test cell (half cell) was prepared in the same manner as that of Example 3-1, and a constant current charging and discharging test was conducted in the same manner as that of Example 3-1. As a result, the initial discharge capacity was 120 mAh/g (the positive electrode capacity). Although charging and discharging were repeated 100 times, results were obtained in which the capacity of the 100$^{th}$ cycle was 91% of the initial capacity.

EXAMPLE 3-4

The lithium borate derivative of Example 2-1 and LiN(SO$_2$CF$_3$)(SO$_2$C$_4$F$_9$) were dissolved in a mixture of ethylene carbonate (EC) and dimethyl carbonate (DMC) (EC:DMC=1:1 by volume) to prepare an electrolytic solution having a lithium borate derivative concentration of 0.95 mol/liter and a LiN(SO$_2$CF$_3$)(SO$_2$C$_4$F$_9$) concentration of 0.05 mol/liter. Then, ion conductivity of the electrolytic solution was measured with an alternating current bipolar-type cell. As a result, the ion conductivity was 6.9 mS/cm at 25° C.

A corrosion test of an aluminum collector was performed in the same manner as that of Example 1-2. When the working electrode was held at 5 V (Li/Li$^+$), there was no flow of current whatsoever. Following testing, although the surface of the working electrode was observed by SEM, there were no changes observed in comparison with that before testing.

The test cell (half cell) was prepared in the same manner as that of Example 3-1, and a constant current charging and discharging test was conducted in the same manner as that of Example 3-1. As a result, the initial discharge capacity was 120 mAh/g (the positive electrode capacity). Although charging and discharging were repeated 100 times, results were obtained in which the capacity of the 100$^{th}$ cycle was 93% of the initial capacity.

EXAMPLE 3-5

A solution was prepared by adding acetonitrile to 70 parts by weight of a polyethylene oxide (average molecular weight: 10,000). Then, 5 parts by weight of the lithium borate derivative of Example 2-1 and 25 parts by weight of LiN(SO$_2$CF$_3$)(SO$_2$C$_4$F$_9$) were added to the solution. The resulting mixture was cast on a glass, followed by drying to remove the acetonitrile. With this, a polymer solid electrolyte film was prepared.

A corrosion test of an aluminum collector was performed using a laminate including the solid electrolyte film interposed between an aluminum electrode (working electrode) and a lithium electrode. This laminate was prepared by press welding. When the working electrode was held at 5 V (Li/Li$^+$), there was no flow of current whatsoever. Following testing, although the surface of the working electrode was observed by SEM, there were no changes observed in comparison with that before testing.

The test cell was prepared in the same manner as that of Example 3-1 except in that the polymer solid electrolyte film was used in place of the electrolytic solution and the separator. In fact, LiCoO$_2$ was used as a positive electrode material to prepare a half cell. A constant current charging and discharging test was conducted at 70° C. under the following conditions. The current density was 0.1 mA/cm$^2$ for both charging and discharging, while charging was performed until 4.2 V and discharging until 3.0 V (vs. Li/Li$^+$). As a result, the initial discharge capacity was 120 mAh/g (the positive electrode capacity). Although charging and discharging were repeated 100 times, results were obtained in which the capacity of the 100$^{th}$ cycle was 91% of the initial capacity.

COMPARATIVE EXAMPLE 3-1

At first, LiN(SO$_2$C$_2$F$_5$)$_2$ was dissolved in a mixture of ethylene carbonate (EC) and dimethyl carbonate (DMC) (EC:DMC=1:1 by volume) to prepare an electrolytic solution having a LiN(SO$_2$C$_2$F$_5$)$_2$ concentration of 1.0 mol/liter.

A corrosion test of an aluminum collector was performed in the same manner as that of Example 1-2. When the working electrode was held at 5 V (Li/Li$^+$), corrosion current was observed. Following testing, the surface of the working electrode was observed by SEM. With this, many pits were observed on its surface. It is assumed that these pits were caused by corrosion.

The test cell (half cell) was prepared in the same manner as that of Example 3-1, and a constant current charging and discharging test was conducted in the same manner as that of Example 3-1. As a result, the initial discharge capacity was 117 mAh/g (the positive electrode capacity). Although charging and discharging were repeated 100 times, results were obtained in which the capacity of the 100$^{th}$ cycle was 69% of the initial capacity.

COMPARATIVE EXAMPLE 3-2

At first, LiN(SO$_2$CF$_3$)$_2$ was dissolved in a mixture of propylene carbonate (PC) and diethyl carbonate (DEC) (PC:DEC=1:1 by volume) to prepare an electrolytic solution having a LiN(SO$_2$CF$_3$)$_2$ concentration of 1.0 mol/liter.

A corrosion test of an aluminum collector was performed in the same manner as that of Example 1-2. When the working electrode was held at 5 V (Li/Li$^+$), corrosion current was observed. Following testing, the surface of the working electrode was observed by SEM. With this, many pits were observed on its surface. It is assumed that these pits were caused by corrosion.

The test cell (half cell) was prepared in the same manner as that of Example 3-1, and a constant current charging and discharging test was conducted in the same manner as that of Example 3-1. As a result, the initial discharge capacity was 112 mAh/g (the positive electrode capacity). Although charging and discharging were repeated 100 times, results were obtained in which the capacity of the 100$^{th}$ cycle was 67% of the initial capacity.

COMPARATIVE EXAMPLE 3-3

At first, LiN(SO$_2$CF$_3$)(SO$_2$C$_4$F$_9$) was dissolved in a mixture of ethylene carbonate (EC) and dimethyl carbonate (DMC) (EC:DMC=1:1 by volume) to prepare an electrolytic solution having a LiN(SO$_2$CF$_3$)(SO$_2$C$_4$F$_9$) concentration of 1.0 mol/liter.

A corrosion test of an aluminum collector was performed in the same manner as that of Example 1-2. When the working electrode was held at 5 V (Li/Li$^+$), corrosion current was observed. Following testing, the surface of the working electrode was observed by SEM. With this, many pits were observed on its surface. It is assumed that these pits were caused by corrosion.

The test cell (half cell) was prepared in the same manner as that of Example 3-1, and a constant current charging and discharging test was conducted in the same manner as that of Example 3-1. As a result, the initial discharge capacity was 118 mAh/g (the positive electrode capacity). Although charging and discharging were repeated 100 times, results were obtained in which the capacity of the 100$^{th}$ cycle was 74% of the initial capacity.

EXAMPLE 4-1

The lithium borate derivative of Example 2-1 and ((CF$_3$)$_2$CHOSO$_2$)$_2$NLi were dissolved in a mixture of ethylene carbonate (EC) and dimethyl carbonate (DMC) (EC:DMC=1:1 by volume) to prepare an electrolytic solution having a lithium borate derivative concentration of 0.01 mol/liter and a ((CF$_3$)$_2$CHOSO$_2$)$_2$NLi concentration of 0.99 mol/liter.

A corrosion test of an aluminum collector was performed in the same manner as that of Example 1-2. When the working electrode was held at 5 V (Li/Li$^+$), there was no flow of current whatsoever. Following testing, although the surface of the working electrode was observed by SEM, there were no changes observed in comparison with that before testing.

The test cell was prepared by the same manner as that of Example 2-1. A constant current charging and discharging test was conducted by the same manner as that of Example 2-1, except that the test was conducted at an environmental temperature of 25° C. The capacity of the 500$^{th}$ cycle was 87% of the initial capacity.

EXAMPLE 4-2

The lithium borate derivative of Example 2-1 and (CF$_3$CH$_2$OSO$_2$)$_2$NLi were dissolved in a mixture of ethylene carbonate (EC) and diethyl carbonate (DEC) (EC:DEC=1:1 by volume) to prepare an electrolytic solution having a lithium borate derivative concentration of 0.90 mol/liter and a (CF$_3$CH$_2$OSO$_2$)$_2$NLi concentration of 0.10 mol/liter.

A corrosion test of an aluminum collector was performed in the same manner as that of Example 1-2. When the working electrode was held at 5 V (Li/Li$^+$), there was no flow of current whatsoever. Following testing, although the surface of the working electrode was observed by SEM, there were no changes observed in comparison with that before testing.

The test cell was prepared by the same manner as that of Example 2-1. A constant current charging and discharging test was conducted by the same manner as that of Example 2-1, except that the test was conducted at an environmental temperature of 60° C. The capacity of the 500$^{th}$ cycle was 84% of the initial capacity.

EXAMPLE 4-3

A lithium borate derivative, represented by the following formula, and $((CF_3)_2CHOSO_2)_2NLi$ were dissolved in a mixture of ethylene carbonate (EC) and ethylmethyl carbonate (EMC) (EC:EMC=1:1 by volume) to prepare an electrolytic solution having a lithium borate derivative concentration of 0.70 mol/liter and a $((CF_3)_2CHOSO_2)_2NLi$ concentration of 0.30 mol/liter.

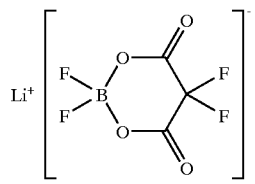

A corrosion test of an aluminum collector was performed in the same manner as that of Example 1-2. When the working electrode was held at 5 V (Li/Li$^+$), there was no flow of current whatsoever. Following testing, although the surface of the working electrode was observed by SEM, there were no changes observed in comparison with that before testing.

The test cell was prepared by the same manner as that of Example 2-1. A constant current charging and discharging test was conducted by the same manner as that of Example 2-1, except that the test was conducted at an environmental temperature of 60° C. The capacity of the 500$^{th}$ cycle was 89% of the initial capacity.

EXAMPLE 4-4

A solution was prepared by adding acetonitrile to 70 parts by weight of a polyethylene oxide (average molecular weight: 10,000). Then, 5 parts by weight of the lithium borate derivative of Example 2-1, and 25 parts by weight of $((CF_3)_2CHOSO_2)_2NLi$ were added to the solution. The resulting mixture was cast on a glass, followed by drying to remove the acetonitrile. With this, a polymer solid electrolyte film was prepared.

A corrosion test of an aluminum collector was performed in the same manner as that of Example 3-5. When the working electrode was held at 5 V (Li/Li$^+$), there was no flow of current whatsoever. Following testing, although the surface of the working electrode was observed by SEM, there were no changes observed in comparison with that before testing.

The test cell was prepared in the same manner as that of Example 2-1 except in that the polymer solid electrolyte film was used in place of the electrolytic solution and the separator. In fact, LiCoO$_2$ was used as a positive electrode material, and a lithium metal foil was used as a negative electrode material.

A constant current charging and discharging test was conducted in the same manner as that of Example 2-5 except that charging and discharging were repeated 100 times. As a result, the initial discharge capacity was 120 mAh/g (the positive electrode capacity). The capacity of the 100$^{th}$ cycle was 92% of the initial capacity.

COMPARATIVE EXAMPLE 4-1

At first, $((CF_3)_2CHOSO_2)_2NLi$ was dissolved in a mixture of ethylene carbonate (EC) and dimethyl carbonate (DMC) (EC:DMC=1:1 by volume) to prepare an electrolytic solution having a $((CF_3)_2CHOSO_2)_2NLi$ concentration of 1.0 mol/liter.

A corrosion test of an aluminum collector was performed in the same manner as that of Example 1-2. When the working electrode was held at 5 V (Li/Li$^+$), corrosion current was observed. Following testing, the surface of the working electrode was observed by SEM. With this, many pits were observed on its surface. It is assumed that these pits were caused by corrosion.

The test cell was prepared in the same manner as that of Example 2-1, and a constant current charging and discharging test was conducted in the same manner as that of Example 2-1, except that the test was conducted at an environmental temperature of 25° C. The capacity of the 500$^{th}$ cycle was 62% of the initial capacity.

COMPARATIVE EXAMPLE 4-2

At first, $(CF_3CH_2OSO_2)_2NLi$ was dissolved in a mixture of ethylene carbonate (EC) and diethyl carbonate (DEC) (EC:DEC=1:1 by volume) to prepare an electrolytic solution having a $(CF_3CH_2OSO_2)_2NLi$ concentration of 1.0 mol/liter.

A corrosion test of an aluminum collector was performed in the same manner as that of Example 1-2. When the working electrode was held at 5 V (Li/Li$^+$), corrosion current was observed. Following testing, the surface of the working electrode was observed by SEM. With this, many pits were observed on its surface. It is assumed that these pits were caused by corrosion.

The test cell was prepared in the same manner as that of Example 2-1, and a constant current charging and discharging test was conducted in the same manner as that of Example 2-1, except that the test was conducted at an environmental temperature of 60° C. The capacity of the 500$^{th}$ cycle was 58% of the initial capacity.

COMPARATIVE EXAMPLE 4-3

At first, the lithium borate derivative of Example 2-1 was dissolved in a mixture of ethylene carbonate (EC) and ethylmethyl carbonate (EMC) (EC:EMC=1:1 by volume) to prepare an electrolytic solution having a lithium borate derivative concentration of 1.0 mol/liter.

The test cell was prepared in the same manner as that of Example 2-1, and a constant current charging and discharging test was conducted in the same manner as that of Example 2-1, except that the test was conducted at an environmental temperature of 60° C. The capacity of the 500$^{th}$ cycle was 65% of the initial capacity.

The entire disclosure of Japanese Patent Applications No. 2000-303437 filed on Oct. 3, 2000, No. 2000-376730 and No. 2000-376731 each filed on Dec. 12, 2000, and No. 2001-177867 filed on Jun. 13, 2001, including specification, claims and summary, is incorporated herein by reference in its entirety.

What is claimed is:

1. An electrolyte for an electrochemical device, said electrolyte comprising a first compound that is an ionic metal complex represented by formula (1),

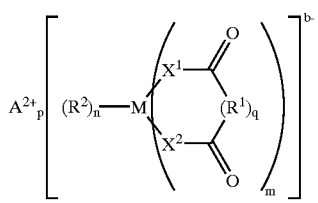

(1)

wherein M is a transition metal selected from the group consisting of elements of groups 3–11 of the periodic table, or an element selected from the group consisting of elements of groups 12–15 of the periodic table;

$A^{a+}$ represents a metal ion, onium ion or hydrogen ion;

a represents a number from 1 to 3; b represents a number from 1 to 3; p is b/a; m represents a number from 1 to 4; n represents a number from 1 to 8; q is 0 or 1;

$R^1$ represents a $C_1$–$C_{10}$ alkylene group, $C_1$–$C_{10}$ halogenated alkylene group, $C_4$–$C_{20}$ arylene group or $C_4$–$C_{20}$ halogenated arylene group, the alkylene and arylene groups of said $R^1$ optionally having substituents and hetero atoms, wherein optionally one of said $R^1$ is bonded with another of said $R^1$;

$R^2$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^3R^3$, the alkyl and aryl groups of said $R^2$ optionally having substituents and hetero atoms, wherein optionally one of said $R^2$ is bonded with another of said $R^2$ to form a ring;

each of $X^1$, $X^2$ and $X^3$ independently represents O, S or $NR^4$; and each of $R^3$ and R4 independently represents a halogen, $C_1$–$C_{10}$ alkyl group, $C_1$–$C_{10}$ halogenated alkyl group, $C_4$–$C_{20}$ aryl group, or $C_4$–$C_{20}$ halogenated aryl group, the alkyl and aryl groups of said $R^3$ and $R^4$ optionally having substituents and hetero atoms, wherein optionally one of is said $R^3$ is bonded with another of said $R^3$ to form a ring, and wherein optionally one of said $R^4$ is bonded with another of said $R^4$ to form a ring.

2. An electrolyte according to claim 1, wherein said M is an element selected from the group consisting of Al, B, V, Ti, Si, Zr, Ge, Sn, Cu, Y, Zn, Ga, Nb, Ta, Bi, P, As, Sc, Hf, and Sb.

3. An electrolyte according to claim 2, wherein said M is an element selected from the group consisting of Al, B and P.

4. An electrolyte according to claim 1, wherein said $A^{a+}$ is a lithium ion, quaternary ammonium ion or hydrogen ion.

5. An electrolyte according to claim 1, further comprising at least one compound selected from the group consisting of compounds represented by the formula $A^{a+}(PF_6^-)_a$, $A^{a+}(ClO_4^-)_a$, $A^{a+}(BF_4^-)_a$, $A^{a+}(AsF_6^-)_a$, $A^{a+}(SbF_6^-)_a$, and formulas (2) to (7),

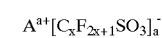
(2)

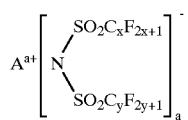
(3)

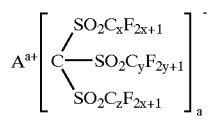
(4)

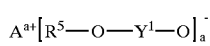
(5)

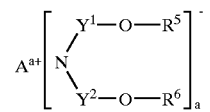
(6)

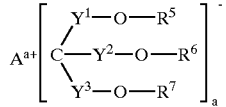
(7)

wherein $A^{a+}$ and a are defined as in the general formula (1);

each of x, y and z independently represents a number from 1 to 8;

each of $Y^1$, $Y^2$ and $Y^3$ independently represents a $SO_2$ group or CO group; and each of $R^5$, $R^6$ and $R^7$ independently represents an electron-attractive organic substituent optionally having a substituent or a hetero atom, wherein optionally at least two of said $R^5$, $R^6$ and $R^7$ are bonded together to form a ring, and wherein optionally at least one of said $R^5$, $R^6$ and $R^7$ is bonded with an adjacent molecule to form a polymer.

6. An electrolyte according to claim 5, wherein said at least one compound is selected from the group consisting of compounds represented by the formulas $A^{a+}(PF_6^-)_a$, $A^{a+}(ClO_4^-)_a$, $A^{a+}(BF_4^-)_a$, $A^{a+}(AsF_6^-)_a$, and $A^{a+}(SbF_6^-)_a$.

7. An electrolyte according to claim 5, wherein said at least one compound is selected from the group consisting of compounds represented by formula (2), formula (3), and formula (4).

8. An electrolyte according to claim 5, wherein said at least one compound is selected from the group consisting of compounds represented by formula (5), formula (6), and formula (7).

9. An electrolyte according to claim 5, wherein a molar ratio of said first compound to said at least one compound is 1:99 to 99:1.

10. An ion conductor for an electrochemical device, said ion conductor comprising:

an electrolyte according to claim 1; and a member selected from the group consisting of a non-aqueous solvent, a polymer and a mixture thereof, said member dissolving therein said electrolyte.

11. An ion conductor according to claim 10, wherein said nonaqueous solvent is an aprotic solvent, and thereby said ion conductor is an electrolytic solution.

12. An ion conductor according to claim 11, wherein said nonaqueous solvent is a mixture of a first aprotic solvent having a dielectric constant of 20 or greater and a second aprotic solvent having a dielectric constant of 10 or less.

13. An ion conductor according to claim 10, wherein said $A^{a+}$ is a lithium ion.

14. An ion conductor according to claim 10, wherein said polymer is an aprotic polymer, and thereby said ion conductor is a solid electrolyte.

15. An ion conductor according to claim 10, which has a concentration of said electrolyte within a range of from 0.1 mol/dm$^3$ to a saturated concentration.

16. An ion conductor according to claim 15, wherein said concentration is within a range of from 0.5 mol/dm$^3$ to 1.5 mol/dm$^3$.

17. An electrochemical device comprising:
(a) first and second electrodes; and
(b) an ion conductor having said first and second electrodes disposed therein, said ion conductor comprising:

(1) an electrolyte according to claim 1; and
(2) a member selected from the group consisting of a nonaqueous solvent, a polymer and a mixture thereof, said member dissolving therein said electrolyte.

18. An electrochemical device according to claim 17, which is a cell or an electrical double-layer capacitor.

19. An electrochemical device according to claim 18, wherein said cell is a lithium cell or a lithium ion cell.

* * * * *